United States Patent
Lanza et al.

(10) Patent No.: US 6,808,704 B1
(45) Date of Patent: *Oct. 26, 2004

(54) METHOD FOR GENERATING IMMUNE-COMPATIBLE CELLS AND TISSUES USING NUCLEAR TRANSFER TECHNIQUES

(75) Inventors: Robert Lanza, Clinton, MA (US); Michael D. West, Boston, MA (US); Jose Cibelli, Holden, MA (US)

(73) Assignee: Advance Cell Technology, Inc., Worcester, MA (US)

( * ) Notice: Subject to any disclaimer, the term of this patent is extended or adjusted under 35 U.S.C. 154(b) by 165 days.

This patent is subject to a terminal disclaimer.

(21) Appl. No.: 09/655,815

(22) Filed: Sep. 6, 2000

Related U.S. Application Data

(60) Provisional application No. 60/155,107, filed on Sep. 22, 1999, and provisional application No. 60/152,354, filed on Sep. 7, 1999.

(51) Int. Cl.[7] .................. A01N 63/00; A61K 39/00; C12N 5/00; C12N 5/04; C12N 15/00

(52) U.S. Cl. .................. 424/93.7; 424/93.1; 424/184.1; 435/325; 435/346; 435/375; 435/377; 800/24

(58) Field of Search .............................. 424/93.1, 93.7, 424/184.1; 435/325, 346, 375, 377, 455, 463, 320.1, 525; 800/24, 3, 18, 21, 22, 25

(56) References Cited

PUBLICATIONS

Dinnyés, A. et al. Somatic Cell Nuclear Transfer: Recent Progress and Challenges. Cloning and Stem Cells, 4:81–90, 2002.*
Hibbs, C.M. et al. Teratomas in Two Calves. Am.J. Vet. Res. 29:1891–1894, 1968.*
Inverdi et al.; Cell Transplantation, 1996, Transplantation Biology: Ce3llular and Molecular Aspects: 679–687.*
Stedman's Medical Dictionary, 1995.*
Anderson et.al.; Development of bovine and porcine embryonic teratomas in athymic mice, 1996, Animal Reproductions Science 45: 231–240.*
Stedman's Medical Dictionary; Electronic Library.*
Inverardi et.al.; Cell Transplantation, 1996, Transplantation Biology: Cellular and Molecular Aspects: 679–687.*
Anderson et,al,; Development of bovine and porcine embryonic teratomas in athytmic mice, 1996, Animal Reproduction Science 45: 231–240.*

* cited by examiner

*Primary Examiner*—Deborah Crouch
*Assistant Examiner*—Thaian N. Ton
(74) *Attorney, Agent, or Firm*—Merchant & Gould LLP; Kristin Chrudimsky

(57) ABSTRACT

This invention relates to methods for making immune compatible tissues and cells for the purpose of transplantation and tissue engineering, using the techniques of nuclear transfer and cloning. Also encompassed are methods for determining the effect on immune compatibility of expressed transgenes and other genetic manipulations of the engineered cells and tissues.

11 Claims, No Drawings

METHOD FOR GENERATING IMMUNE-COMPATIBLE CELLS AND TISSUES USING NUCLEAR TRANSFER TECHNIQUES

This application claims the benefit of U.S. Provisional Patent Application No. 60/152,354 filed Sep. 7, 1999 and U.S. Provisional Patent Application No. 60/155,107 filed Sep. 22, 1999.

FIELD OF INVENTION

The present invention combines the fields of cloning, developmental biology and tissue engineering to devise immune compatible tissues and cells for the purpose of transplantation. In addition, the invention discloses methods of generating therapeutic cells and tissues for transplantation using nuclear transfer techniques, and methods of verifying or evaluating the immune compatibility of such tissues.

BACKGROUND OF INVENTION

The past decade has been characterized by significant advances in the science of cloning, and has witnessed the birth of a cloned sheep, i.e. "Dolly" (Roslin Bio-Med), a trio of cloned goats named "Mira" (Genzyme Transgenics) and over a dozen cloned cattle (ACT). The technology which enables cloning has also advanced such that a mammal may now be cloned using the nucleus from an adult, differentiated cell, which scientists now know undergoes "reprogramming" when it is introduced into an enucleated oocyte. See U.S. Pat. No. 5,945,577, herein incorporated by reference in its entirety.

The fact that an embryo and embryonic stem cells may be generated using the nucleus from an adult differentiated cell has exciting implications for the fields of organ, cell and tissue transplantation. There are currently thousands of patients waiting for a suitable organ donor, and face problems of both availability and incompatibility in their wait for a transplant. If embryonic stem cells generated from the nucleus of a cell taken from a patient in need of a transplant could be made and induced to differentiate into the cell type required in the transplant, then the problem of transplantation rejection and the dangers of immunosuppressive drugs could be precluded.

Embryonic stem cells have been induced to develop into cells from the three different germ layers. For instance, Anderson et al. demonstrated that inner cell masses (ICM) and embryonic discs from bovine and porcine blastocysts will develop into teratomas containing differentiated cell types from ectodermal, mesodermal and endodermal origins when transplanted under the kidney capsule of athymic mice. *Animal Repro. Sci.* 45: 231–240 (1996). Furthermore, the developmental signals that trigger cell differentiation are beginning to be deciphered. For instance, Gourdie et al. demonstrated the differentiation of embryonic myocytes into impulse-conducting Purkinje fiber cells. *Proc. Natl. Acad. Sci. USA* 95: 6815–6818 (June, 1998). Further, researchers at the University of Medicine and Dentistry of New Jersey (UMDNJ) have recently reported the transformation of bone marrow cells into nerve cells (Washington Post, Aug. 15, 2000, p. A6). Thus, it should be possible to isolate differentiated cells from embryonic stem cells or teratomas, and induce their differentiation into particular cell types for use in transplantation.

In addition, by using techniques evolving in the field of tissue engineering, tissues and organs could be designed from the differentiated cells, which could be used for transplantation. For instance, Shinoka et al. have designed viable pulmonary artery autografts by seeding cells in culture onto synthetic biodegradble (polyglactinlpolglycolic acid) tubular scaffolds. *I. Thorac. Cardiovasc. Surg.* 115: 536–546 (1998). Zðnd et al. demonstrated that seeding of human fibroblasts followed by endothelial cells on resorbable mesh is helpful for creation of human tissues such as vessels or cardiac valves. *Eur. J. Cardic-Thorac. Surg.* 13: 160–164 (1998). Freed et al. have shown that culturing cells under conditions of simulated microgravity is advantageous for the engineering of cartilage and heart tissue. In Vitro Cell Dev. Bid.—Animal 33: 38 1–385 (May, 1997).

However, the fields relating to cell development and differentiation, and tissue engineering have deficiencies. For instance, the teratomas created by Anderson et al. were created from naturally-formed embryos. Thus, the genotype of the embryos will be unique to the individual embryos. Such cells are not appropriate for transplantation, because they would still induce transplant rejection just as any allogeneic tissue when transplanted into a donor animal. Most autograft tissue engineering studies, in contrast, have been performed using cells from the actual recipient animal. Such a technique will not provide suitable transplant organs to those patients whose cells or organs are deficient, i.e., perhaps for lack of gene expression, or due to expression of a mutant gene. Moreover, for a patient whose organ has literally shut down, it will not be possible to engineer a new organ from the patient's own cells. Thus, there are many deficiencies to be overcome in applying the concepts of cellular differentiation and development and tissue engineering to the treatment of transplant patients.

SUMMARY OF INVENTION

The present invention addresses the uncertainties still to be overcome in the use of engineered cells and tissues for transplantation. The invention discloses methods of engineering cloned, immune compatible, developmentally differentiated cells into tissues for transplantation, and methods of using such tissues to treat a patient in need of a transplant. In particular, such tissues maybe designed to express a therapeutic protein. Because the tissues and cells for transplantation are all generated from the same original donor cell through nuclear transfer, all the cells of the engineered tissue will express the heterologous gene of interest. The methods of the invention therefore additionally provide an invaluable alternative to tissue-targeted gene therapy.

The present invention also provides methods for determining whether particular genetically engineered cells will provide immune compatible organs for transplantation. For instance, the present invention discloses methods of evaluating cloned cells for mitochondrial compatibility, and in particular, transgenic, developmentally differentiated cells, for immune compatibility in an animal model. Such evaluations will provide important information regarding tie suitability of therapeutic tissues in transplantation, and will provide the foundation for controlling these parameters in order to provide immune compatible tissues.

DETAILED DESCRIPTION

The present invention is directed to methods of producing of immune compatible tissues using cloning technology. The cells and engineered tissues produced by the disclosed methods are also encompassed in the present invention, as are the stable grafts produced by transplantation of the engineered tissues. A stable graft is defined as a graft that does not illicit an immune response or rejection when transplanted into a nuclear donor, or at least provides a substantial improvement in avoiding graft rejection over non-cloned control transplanted tissue. Because cloned cells generated by nuclear transfer are not completely identical with the donor cell or animal, e.g., they typically lack the mitochondrial DNA of the donor cell and gain the mitochondrial DNA of the recipient enucleated oocyte or other cell and typically are not produced in an in vivo environment that will perfectly mimic conditions present during embryogenesis, the question is raised as to whether such cells will be entirely immune-compatible when they are transplanted back into the donor animal.

For instance, it has been demonstrated that mitochondrial peptides in mice, e.g., the ND1 peptide from the amino terminus of NADH dehydrogenase and the MiHA peptide encoded by the amino terminus of the COI gene, are presented at the cell surface by non-classical MHC class I molecules, e.g., H-2M3a, in combination with beta-2-microglobulin (Vyas et al., 1992, "Biochemical specificity of H-2M3a . . . ," *J. Immunol.* 149(11):3605–11; Morse et al., 1996, "The COI mitochondrial gene encodes a minor histocompatibility antigen presented by H2-M3," J. Immunol. 156(9): 3301–7). It has also been shown that allelic variation at a single residue in the ND1 peptide renders cells displaying foreign alleles susceptible to lysis by specific cytotoxic T cells (Loveland et al. 1990. 60(6): 971–80). A similar system has been identified in rats, although the mitochondrial peptide which is responsible for histocompatibility in the rat is not the same as the allelic ND1 peptide from mice (Davies et al., 1991, "Generation of T cells with lytic specificity for atypical antigens. I. A mitochondrial antigen in the rat," J. Exp. Med. 173: 823–32).

Thus, mitochondrial peptides displayed at the cell surface can serve as histocompatibility antigens, seeing as two separate systems have been identified in mice and rats, respectively. There is no reason to believe that similar systems would not be present in other mammals. Therefore, foreign mitochondria would be expected to result in the rejection of therapeutic tissue generated by nuclear transfer technology. Instead, using the methods of the present invention, the present inventors have surprisingly found in performing the methods of the present invention that nuclear transfer generated cells having allogeneic mitochondria are not rejected when transplanted into the nuclear donor.

Despite the fact that cloned tissues having allogeneic mitochondria were not rejected after transplant, the question of transplant compatibility becomes even more relevant when such cells are transfected with a transgene or undergo some other genetic manipulation in order to modify, supplement or bolster the function of the transplanted tissue. Accordingly, the present invention provides methods and animal models for testing the immune compatibility of cloned cells or tissues in an animal model, and for enhancing the immune compatibility of such cells or tissues as needed. Generally, such methods comprise:

a. obtaining a cell from a donor animal;
 b. transferring the nucleus from said cell into a recipient oocyte or other suitable recipient cell to generate an embryo and optionally introducing a therapeutic heterologous DNA;
 c. isolating an embryonic disc, inner cell mass, and/or stem cell from said embryo;
 d. injecting said disc and/or stem cell into said donor animal at the same time as control embryonic disc and/or stem cell; and
 e. examining the injection sites for teratoma formation, and signs of subsequent rejection.

For the purposes of the present invention, a teratoma is defined as a group of differentiated cells containing derivatives of mesoderm, endoderm, or ectoderm resulting from totipotent cells. A control embryonic disc, inner cell mass, or stem cell is one which was not generated using a donor cell from the test animal (allogeneic or xenogeneic nuclear DNA), and therefore, the teratoma thus generated from such disc or cell is expected to be rejected in the donor animal, or alternatively, may never develop at all. Teratomas generated using a nucleus from the donor animal (isogenic) and an allogeneic recipient oocyte or other suitable recipient cell would also be expected to be rejected when used in transplantation due to presentation of mitochondrial alleles as histocompatibility antigens. Thus, the fact that such therapeutic tissues do not lead to transplant rejection is truly surprising indeed.

Donor and control embryonic discs, inner cell mass, and/or stem cells are generally injected intramuscularly, introduced under the renal capsule, subcutaneously or into the paralumbar fascia Where a teratoma is formed, it is removed and examined for the presence of germ layers, which may further be separated for the purpose of detecting or isolating specific cell types. While teratoma formation may give an initial indication of immune compatibility, specific cell types may be generated and re-introduced into the donor animal to further test immune compatibility, particularly where the transfected-heterologous gene is expressed from a cell-type specific promoter. Given that the cloned tissues of the present invention having allogeneic mitochondria were not rejected, this system is ideal for testing the affect of a transgene on tissue compatibility whereby the cell from said donor animal is transfected with a heterologous gene prior to nuclear transfer.

Generally, the methods of the invention may be performed using any cell from the donor animal. Suitable cells include by way of example immune cells such as B cells, T cells, dendritic cells; skin cells such as keratinocytes, epithelial cells, chondrocytes, cumulus cells, neural cells, cardiac cells, esophagial cells, primordial germ cells, cells of various organs including the liver, stomach, intestines, lung, kidneys, etc. In general the most appropriate cells are easily propagatable in tissue culture and can be easily transfected. Preferably, cell types for transfecting heterologous DNA and performing nuclear transfer are fibroblasts.

The animal model may be any animal suitable for generating teratomas and studying immune compatibility. A preferred animal is an ungulate, and more preferred is a bovine. Alternatively, the animal may be a non-human primate, e.g., a baboon or cynomolgus monkey. Large animals are preferred because they may give rise to larger teratomas, thereby providing more cells for immunological evaluation and for transplantation. Suitable animals include by way of example pigs, dogs, horses, buffalo and goats Also included in the present invention are methods of testing the immune compatibility of cloned teratomas in cross-species animal models, e.g., where the nucleus of the donor species is inserted into a recipient oocyte or other suitable recipient cell of another species (xenogeneic). Cloned teratomas having the mitochondria from the recipient cell may then be tested for immune compatibility by injecting an embryonic disc, inner cell mass, and/or stem cell into the donor animal. Particularly preferred are cross-species models involving closely related species, where the mitochondrial proteins of the recipient cell would be expected to function in combination with the donor nucleus.

For instance, according to a report in the New York Times on Nov. 12, 1998 (Nicholas Wade, "Human Cells Revert to Embryo State, Scientists Assert"), although cow mitochondria would not be expected to work with a human nucleus, the mitochondria of chimpanzees and gorillas would be expected to be functional in human cells. In fact, scientists have already made chimeric "geep" (combined sheep and goat), and "camas" (combined camels and lamas), suggesting that the cells and cellular organelles of closely related species would be functionally compatible (see Ruffing et al., Biol. Reprod. (1993) 48(4):889–904; also "Bush telegraph on chimeras," The Daily Telegraph, Jan. 22, 1998, p. 27; "It's a geep: cross-breeding goats and sheep," *Time*, Feb. 27, 1984, p. 71; "Meet the geep: part goat—part sheep," *Science*, May 1984, 5: 6). According to Jakovcic et al. (1975, "Sequence homology between mitochondrial DNAs of different eukaryotes," *Biochem.* 14(10): 2043–50), evolutionary divergence of mtDNA sequences appears to have occurred at rates similar to that for unique sequence nuclear DNA.

Such cross-species models have particular relevance to the study of xenotransplantation, and would provide a convenient model for identifying the mitochondrial proteins that serve as histocompatibility antigens. If the mitochondria of the recipient cell prove to be functionally, but not immunologically, compatible using the teratoma model, it will be possible to identify mitochondrial antigens and peptides which are displayed on the cell surface but may not exhibit allelic variation within a single species. Such a model will facilitate recombinant DNA methodology geared toward replacing the relevant mitochondrial antigens in the recipient cell with those from the nuclear transfer donor, in order to further enhance the immune compatibility of the cloned cells and tissues for trasplantation therapy.

For instance, if cloned "cross-species" teratomas also show signs of rejection, steps may be taken in accordance with the invention to ensure that cloned cells and tissues are compatible with the nuclear donor, for instance, by selecting recipient cells which express compatible mitochondrial antigens, or by replacing the histocompatible mitochondrial epitopes. In fact, one group of researchers has reported complete replacement of endogenous mitochondrial DNA in one Drosophila species with the mitochondrial DNA of another (Niki et al. 1989. Complete replacement of mitochondrial DNA in Drosophila Nature 341(6242): 551–2. Thus, it should be possible to engineer recipient cells that have a desired mitochondrial phenotype for any particular nuclear transfer donor, or even a mixture of mitochondrial phenotypes, i.e., isogenic and allogeneic, or isogeneic and cross-species.

Mitochondrial genes or DNA segments responsible for mitochondrial antigen histocompatibility, particularly in cross-species models, may be readily identified using the methods of the present invention. For instance, isogenic nuclei from a designated mammalian nuclear donor can be transferred into different allogeneic mitochondrial backgrounds of a closely related species, and such cells may be used to immunize the nuclear transfer donor in order to isolate and identify antibodies and lymphocytes specific for mitochondrial epitopes. By comparing the specificities of the panels of antibodies and lymphocytes achieved by immunizing the nuclear donor, it is possible to identify mitochondrial antigens and epitopes that result in immune recognition and possibly graft rejection in cross-species models. Identification of such mitochondrial antigens and epitopes will allow replacement of the corresponding encoding DNA, such that transplant rejection of cross-species nuclear transfer generated cloned tissues may be avoided.

Thus, the present invention includes methods of identifying mitochondrial histocompatibility antigens using cross-species nuclear transfer, comprising:

obtaining cells from a donor mammal;
transferring nuclei from said donor mammal into at least two recipient oocytes or other suitable recipient cells of a mammalian species other than said nuclear donor to generate embryos, wherein said at least two recipient cells are allogeneic with regard to mitochondrial DNA;
isolating embryonic discs and/or stem cells-from said embryos;
injecting said discs and/or stern cells separately back into said donor mammal as to generate a specific panel of antibodies and/or lymphocytes; and
comparing panels of antibodies and/or lymphocytes generated in response to said allogeneic mitochondrial backgrounds in order to identify mitochondrial antigens and/or epitopes that are recognized by the immune system of said donor mammal.

Antibodies and lymphocytes (both helper and cytotoxic T-cells and B-cells) specific for the mitochondrial antigens identified in such methods are also encompassed by the present invention, as are the mitochondrial peptides, antigens, and DNAs or DNA fragments encoding the same.

The ability to re-clone cloned mammals and generate a line of cloned mammals that are isogenic for both nuclear and mitochondrial DNA allows for concurrent injection of the cross-species cloned cells containing allogeneic mitochondria into separate mammals, thereby facilitating the retrieval of panels of antibodies and lymphocytes specific for different mitochondrial backgrounds. Methods of recloning cloned mammals based on the observation that nuclear transfer can be used to rejuvenate senescent cells are disclosed in commonly assigned, copending application Ser. No. 09/656,173, filed concurrently herewith and incorporated by reference in its entirety. Of course, it is also possible to generate cloned mammals having isogenic mitochondrial DNA by performing nuclear transfer from a single donor using multiple oocytes or other suitable recipient cells from a single recipient mammal or cell line. Thus the methods of the present invention may also be performed wherein said discs and/or stem cells are injected into separate mammals which are isogenic to the nuclear donor with respect to both nuclear and mitochondrial DNA in order to isolate panels of antibodies and/or lymphocytes.

The present invention also encompasses methods of generating therapeutic cloned tissue for transplant which express a heterologous protein. The heterologous DNAs to be used in the methods of the present invention may encode a therapeutic protein to be expressed in a transplant recipient, but may also be a reporter gene for the purpose of monitoring gene expression in the teratoma. The reporter gene may be any which is convenient for monitoring gene expression, but is preferably selected from the group consisting of green flourescent protein (GFP), beta-galactosidase, luciferase, variants thereof, antibiotic resistance markers, or other markers.

Also, the use of tissue-specific promoters or tissue specific enhancers provides a means of selecting for expression of heterologous DNAs in desired tissue types. Alternatively, the cells may be selected based on the expression characteristics of cell surface markers. For example, hematopoietic stem cells may be selected based on CD34 expression.

While the donor cell may also contain deletions and insertions into the genome that disrupt or modify the expression of native genes, preferably the donor cell is transfected with a heterologous gene that encodes a protein that is secreted and performs a therapeutic function in the intended transplant recipient, i.e., replaces a native gene which is mutated, or is not expressed. Where it is found that the expressed protein generates an immune response, the animal used in the animal model to test immune compatibility may then be used for the evaluation of the immune response and the isolation of antibodies or cytotoxic T cell clones.

The teratomas generated in animals used to test immune compatibility of cloned tissues will also be useful for the study of molecular signals that control cell differentiation and development. For instance, reporter gene constructs designed with putative developmental promoters, enhancers, repressors or other gene control sequences may be inserted into the donor nucleus prior to nuclear transfer, and the teratomas may then be monitored visually or by other means to see at which stage reporter gene expression is turned on.

As described above, the differentiated teratoma cells may be separated and used to individually test the immune compatibility of a particular cell or tissue. Once a particular cell type of interest is identified, it may be used to engineer a tissue using the methods described herein and known in the art. The animal models disclosed find particular use in testing new matrix materials in tissue engineering for immune compatibility. Preferred engineered tissues of the present invention are selected from the group consisting of smooth muscle, skeletal muscle, cardiac muscle, skin, kidney and nervous tissue.

Thus, the present invention also concerns methods of generating immune compatible tissues for trasplantation, comprising:

a. obtaining a donor cell from an intended transplant recipient;

b. transferring the nucleus from said cell into a recipient oocyte or other suitable recipient cell to generate an embryo;

c. isolating an embryonic disc, inner cell mass, and/or stem cell from said embryo;

d. injecting said disc, inner cell mass, and/or stem cell into an immune compromised animal;

e. isolating the resulting teratoma;

f. isolating from the teratoma a cell of the type required for transplantation, and optionally expanding said cells in vitro using a growth factor; and g. engineering a tissue from said cells or combinations of cells.

It will also be possible as the signals for cell differentiation and development are identified to produce the desired cell types for tissue engineering and transplantation without prior teratoma formation, because the development of particular cell types will be directed in vitro. Alternatively, at least with mammals other than humans, it is currently possible to acquire cloned tissues directly from growing embryos or fetuses rather than generate a teratoma. Humans may be next, however, at least for harvesting cell types that develop during the first two weeks of embryogenesis, if a recent recommendation by a high ranking British science and ethics commission results in legislation (see Weiss, "British panel urges allowing human embryo cloning," The Washington Post, page A26, Aug. 17, 2000).

Tissue engineering may be effected, e.g., using three-dimensional scaffolds or biodegradable polymers such as are used in the construction of dissolvable sutures. Such methods have been well reported in the patent and non-patent literature by companies such as Tissue Engineering, Inc. and Organogenesis. Examples of patents and references in the area of tissue engineering include U.S. Pat. Nos. 5,948,429, 5,709,934, 5,983,888, 5,891,558, 5,709,934, 5,851,290, 5,800,537, 5,882,929, 5,800,537, 5,891,558, 5,709,934, 5,891,617, 5,518,878, 5,766,937, 5,733,337, 5,718,012, 5,712,163, and 5,256,418, all of which are incorporated by reference in their entirety. Also, reference is made to numerous patents and literature references by Robert Langer and John Vacanti, who are both prolific in the area of tissue regeneration research. As discussed in many of there patents, it may be desirable to include biologicals that facilitate blood tissue development, i.e., growth factors and other compounds that promote angiogensis.

In particular, the immune-compatible tissues and cells generated are useful in methods of providing a patient in need of a transplant with an immune-compatible transplant. Such a method further comprises, in addition to the above steps, transplanting said engineered tissue into a patient. The fact that the present inventors have surprisingly found that cloned cells containing isogenic nuclear DNA and allogeneic mitochondrial DNA do not induce transplant resection has particular relevance for transplants which replace native cells suffering from mitochondrial damage, for instance as in amyotrophic lateral sclerosis (ALS), or Leber's hereditary optic neuropathy (LHON). In such cases, cloned tissue having isogenic nuclear DNA and allogeneic mitochondrial DNA that does not induce an immune reaction is the most ideal tissue for transplantation in that such tissue not only provides the closest histocompatibility match, but it also effectuates mitochondrial gene therapy in that tissue containing damaged mitochondria is replaced.

For instance, Dhaliwal and colleagues recently demonstrated that brain tissue from patients with ALS had a thirty-fold higher incidence of the "common mutation," which is a 4977 base-pair mutation deletion observed in various tissues of patients with mitochondrial and other disorders ("Mitochondrial DNA deletion mutation levels are elevated in ALS brains," Mol. Neurosci. 11(113): 2507–9). In fact, an accumulation of mtDNA$^{4977}$ has been observed in the brains, hearts and muscles of healthy older individuals suggesting a contribution to the aging process in these tissues (Soong and Amheim, 1995, Methods Neurosci. 26: 105–28). Thus, cloned tissues having allogeneic "young" mitochondrial DNA might provide an advantage over the patient's own cells by virtue of the absence of age-related mitochondrial mutations.

Mitochondrial DNA is believed to be more susceptible to age-related mutations than is genomic DNA because of the relative lack of DNA repair mechanisms and histones (Dhaliwal et al. 2000). However, there are also hereditary mitochondrial mutations transmitted maternally that manifest themselves in particular tissues, that would benefit by the cloning and tissue engineering techniques in the present application.

For instance, Leber's hereditary optic neuropathy (LHON) is a rare disorder of the optic nerve that causes legal blindness in most patients that it affects. It is caused by a mutation in the mitochondrial DNA that is passed maternally, however, the disease typically manifests itself later in life (sudden loss of vision in the first eye typically occurs at the age of 10–50) (Zickermann et al., 1998, "Analysis of the pathogenic human mitochondrial mutation ND1/3460, and mutations of strictly conserved residues in its vicinity . . . ," Biochem. 37(34): 11792–6). Researchers at the Molecular Ophthalmology Laboratory at the University of Iowa have developed an improved method for detecting the mutation, which is used to diagnose LHON.

The cloning, tissue engineering, and transplantation techniques of the present invention will be especially valuable for replacing diseased tissue linked to mitochondrial mutations in that the cloned tissues will typically possess isogenic nuclear DNA, but allogeneic mitochondrial DNA.

Therefore, for instance, engineered nervous tissue for transplantation into LHON patients will effectuate gene therapy of the mitochondrial DNA while at the same time, replace the diseased optic nerve tissue.

As described above, said donor cell may be genetically altered prior to nuclear transfer by the transfection of at least one heterologous gene, or the disruption or replacement of at least one native gene. Such a genomic modification is particularly useful where the transplant recipient's own genome fails to express a required protein, or expresses a mutated protein such that the original tissue or organ failed to function properly. Alternatively or additionally, if prior tests of immune compatibility suggest some rejection is anticipated, e.g., due to allogeneic or xenogeneic differences in mitochondrial DNA, the donor cell may be transfected with genes expressing proteins that deter or decrease immune rejection prior to nuclear transfer.

The methods of the present invention are particularly useful for repairing and replacing tissues damage by autoimmune diseases due to the aberrant expression of self-peptides. For instance, primary biliary cirrhosis (PBC) is a chronic autoimmune liver disease characterized by progressive inflammatory obliteration of the intrahepatic bile ducts ultimately leading to cirrhosis (Melegh et al., 2000, "Autoantibodies against subunits of pyruvate dehydrogenase and citrate synthase in a case of paediatric biliary cirrhosis," Gut 2: 753–6). The disease is characterized by decreased tolerance to self mitochondrial proteins, and is associated with high titers of anti-mitochondrial antibodies, which may be detected using techniques known in the art (Leung et al., 1991, "Use of designer recombinant mitochondrial antigens in the diagnosis of primary biliary cirrhosis," Hepatol. 15(3): 367–72). Liver transplantation has become the treatment of choice with patients with advanced disease (Sebagh et al., 1998, "Histological features predictive of recurrence of primary biliary cirrhosis after liver transplant," Transplantation 65(10): 1328–33).

The anti-mitochondrial antibodies in PBC typically recognize a restricted epitope on the E2 subunit of the pyruvate dehydrogenase complex (PDC), which is a nuclear encoded protein which is normally transported into the mitochondria and loosely associated with the inner membrane. Although the PDC protein is normally shielded from the immune system, patients having PBC have been shown to express PDC-E2 on the surface of biliary epithelial cells (Joplin et al., 1992, "Distribution of dihydrolipoamnide acetyltransferase (E2) in the liver and portal lymph nodes of patients with primary biliary cirrhosis: an immunohistochemical study," Hepatology 14: 442–7). Thus, one theory as to how PBC is initiated is that a nuclear genetics alteration affects the transport of PDC-E2 to the mitochondria, i.e., such as mutations in the leader sequence that direct E2 to the outer membrane (Björkland and Tötterman, 1994, "Is primary biliary cirrhosis an autoimmune disease?" Scand. J. Gastroenterol. 29 Suppl. 204: 32–9).

Thus, in the case of PBC, the nuclear transfer-generated cells can be corrected for the nuclear defects that lead to the autoimmune disease prior to generation of the liver cells and tissues for trasplantation, i.e., by replacing the mutated leader sequence. As a result, the cloned cells and tissues used for transplantation into a PBC patient would not only provide the closest immune compatible tissue to avoid rejection, but also effectuate gene therapy which repairs a nuclear gene linked to the autoimmune disease itself. The methods of the present invention are equally as valuable for the transplantation and gene therapy of any diseased tissue where the nuclear mutations associated with the disease process have been identified, e.g., for the treatment of bums, blood disorders, cancer, chronic pain, diabetes, dwarfism, epilepsy, heart disease such as myocardial infarction, hemophilic, infertility, kidney disease, liver disease, osteoarthritis, osteoporosis, stroke, affective disorders, Alzheimer's disease, enzymatic defects, Huntington's disease, hypocholesterolemine, hypoparathyroidase, immunodeficiencies, Lou Gehrig's disease, macular degeneration, multiple sclerosis, muscular dystrophy, Parkinson's disease, rheumatoid arthritis, and spinal cord injuries.

In this regard, it is pertinent to note that the present inventors have also discovered that the cloning procedures of the present invention enables the rejuvenation of senescent cells, thereby foregoing any concerns regarding the genetic age of cloned tissues. The disclosure of U.S. application Ser. No. 09/656,173, which is co-owned with the present application, reports the inventors' surprising observations relating to the rejuvenation of primary cells using nuclear transfer, and is herein incorporated in its entirety. The finding that the cloning process rejuvenates older cells is particularly relevant for designing therapeutic tissues expressing more than one heterologous gene, or having more than one gene knocked out, because such tissues can be generated by cloning and re-cloning primary cells of the same genetic background.

It is also possible to effectuate changes to the mitochondrial DNA of the recipient cell using techniques known in the art (see Wheeler et al. 1997. Modification of the mouse mitochondrial genome by insertion of an exogenous gene. Gene 198(1–2): 203–9; Yamaoka et al. 2000. Complete repopulation of mouse mitochondrial DNA-less cells with rat mitochondrial DNA . . . Genetics 155(1): 301–7). This may be helpful for generating immune compatible cells and tissues for transplantation, particularly in the case where mitochondrial antigens are displayed by the cloned cells, and generate an immune response when the cloned cells are transplanted back into the nuclear donor. Alternatively, if pretesting shows that transplant rejection due to mitochondrial DNA differences is anticipated, particularly in the case of xenogeneic mitochondria, the suitable recipient cell may be particularly selected based on mitochondrial compatibility.

Although any animal may benefit from the cells and tissues generated by the disclosed methods, a preferred transplant recipient is a human. When the intended transplant recipient is a human, teratomas may be formed following nuclear transfer, i.e., of a fibroblast nucleus, from said human into any human recipient oocyte, because it is the genome of the donor (intended transplant recipient) that reprograms the cell for development. Teratomas generated from human nuclear donors and recipients may be formed in and isolated from an immune compromised animal, such as a skid or nude mouse.

As described above, the teratomas generated may be removed and examined for the formation of germ layers, and such germ layers may be further separated or differentiated into distinct cell types. Distinct cell types may then be used to engineer tissues for transplantation. Preferably, said tissues are selected from the group consisting of smooth muscle, skeletal muscle, cardiac muscle, skin, kidney and nervous tissue. Also encompassed are the tissues and cells generated by the disclosed methods.

The concept of human "therapeutic cloning" is to transfer the nucleus from one of the patient's cells, i.e., a fibroblast cell, into an enucleated recipient oocyte or other suitable recipient cell. After reprogramming, the donated somatic nucleus regains its totipotency and is able to initiate a round of embryonic development. Pluripotent stem cells derived from the resulting embryo carry the nuclear genome of the patient, and are then induced to differentiate into replacement cells, such as cardiomyocytes to replace damaged heart tissue, insulin-producing n-cells for patients with diabetes, chrondrocytes for osteoarthritis, or dopaminergic neurons to treat Parkinson's disease.

The methods of the invention should eliminate or at least substantially alleviate the immune responses associated with transplantation of these various tissues, and therefore abrogate the requirement for immunosuppressive drugs, such as cyclosporine, imoran, FK-506, glucocorticoids, and variants thereof, which carry the risk of a wide variety of serious complications, including cancer, infection, renal failure and osteoporosis. However, at least in some instances, it may still be advisable to utilize anti-rejection agents at least initially. As discussed above, the transplanted cells may not be immunologically identical to the transplant recipient's cells, even though the nucleus of one of the recipient's cells served as the donor. This could be caused by mitochondrial DNA differences particularly in the case of xenogeneic, mitochondria, or antigenic differences that may result from transfected heterologous DNA or because of the artificial environment used to affect nuclear transfer. In particular, such an environment does not mimic identically the cellular environment that exits during embryonic development.

For example, it is known that cells cultured for prolonged periods may be antigenically different as a result of culturing (a phenomenon known as "antigenic drift"). Therefore, it may still be desirable to tolerize the cells or tissues prior to transplantation, e.g. by treatment with soluble CD40, CD40-ligand antagonists, low temperature culture, use of antibodies that mask donor antigens, or by expression of UV light (e.g., islets).

Although not limiting, the scope and spirit of the invention are illustrated by reference to the following discussion and examples.

EXAMPLE 1

This experiment was designed to test the immune compatibility of a nuclear transfer-generated cells in a pre-clinical large animal model: cattle (Bos taurus).

Three adult Holstein steers approximately 8–10 months old (weighing approximately 500–1000 lbs) were purchased from Thomas Morris, Inc., Maryland, and shipped to the South Deerfield Farm at the University of Massachusetts, Amherst. To obtain fibroblasts for nuclear transfer, skin biopsies were obtained from each of the animals by ear notch. A plasmid which expresses a reporter gene encoding enhanced green fluorescent protein (eGFP) was transfected into the cells, and transfected cells were selected with neomycin. Purified cells, analyzed by PCR and/or FISH, were used for nuclear transfer as described previously in Nature (1998) Biotechnol. 16: 642–646, herein incorporated by reference.

Isolated embryos having at least one cell, or embryonic discs/inner cell mass or stem cells generated from bovine blastocysts/stem cells are then injected into the paralumbar fascia of the donor steers (two sites with experimental (same animal) stem cells, two sites with experimental (same animal) embryonic discs, two sites with inner cell mass, and four sites with control (different animal) stem cells, per animal). After two months, the muscle is examined for teratoma formation. Any tumors identified are removed for histological analysis.

The procedure is performed on the standing animal using 20 mg Xylazine/8 mg Butorphanol Tatrate administered IV in the tail vein. The paralumbar fascia area is clipped and surgically prepared, using 100 ml of 2% Lidocaine as a local anesthetic administered as a paralumbar block. The animals should be given antibiotics for three days post-surgically as a precautionary measure (Cefilofur Hcl 50 mg/cc @ 1 cc/100 pounds). Immediately following surgery a single injection intramuscularly or under the kidney capsule of Flunixin Meglumine @ 1 cc/100 pounds may be given to control pain and swelling at the surgical site. If teratoma formation does not occur at the paralumbar fascia, other sites may be analyzed, i.e,. subcutaneously.

It is expected that "same animal" stem cells will survive in the recipient (donor of nucleus) animal in contrast to "different animal" stem cells, or survive at least better or longer depending on the cytotoxic T cell response or other immune reaction to foreign mitochondrial peptides. Furthermore, it is expected that cells from all three germ layers, i.e., ectoderm, mesoderm, and endoderm, will be observed in "same animal" teratomas.

EXAMPLE 2

This example was designed to test teratoma formation in an immune-compromised animal model. This example is relevant to the methods whereby cloned, nuclear transfer-generated cells from a patient in need of a transplant may be grown in a SCID mouse or other immune-compromised animal in order to generate differentiated cells for isolation and design of engineered tissues for transplant.

ES cells transfected with GFP were derived from two adult Holstein steers (two different ES cell lines were derived from each animal). ICMs were derived from 12-day-old blastocysts.

Cell Preparation and Injection Procedure:

Cells were cut into pieces (sections of no more than about 100 cells each) and loaded into a 1 ml syringe, no more than 200 microliters each, and preferably 100 microliters.

ICMS were mechanically isolated and loaded into a 1 ml syringe 100 to 150 microliters.

Cells were kept at room temperature in HECM-Hepes.

Twenty-two-gauge needles were used for injection procedures. Cells were injected into the skeletal muscle of the hind leg of SCID mice.

| Mouse # | Treatment | Amount | Observations |
|---|---|---|---|
| 1 | ICM day 14 from cow #25 | 6 | 100 |
| 2 | ICM day 14 from cow #22 | 9 | 3 ICMs were found left inside the syringe |
| 3 | Monkey cross-species (into bovine) 4–8 cell embryos | 90 | — |
| 4 | ES 22.B | One plate (30 mm) | — |
| 5 | ES 22.B | Three plates | — |
| 6 | ES 22.C | One plate | — |
| 7 | ES 22.C | Three plates | — |
| 8 | ES 25.E | One plate | — |
| 9 | ES 25.E | Three plates | — |
| 10 right | ES 25.F | One plate | — |
| 10 left | ES 25.F | Three plates | — |

Bovine stem cells and ICMs that were injected into the skeletal muscle of the SCID mice were retrieved after 7–8 weeks (although it is possible to let the cells go longer, or remove them sooner). A small nodular lesion was identified in two of the mice which received ES cell injections (mice#s 7 and 9).

Gross Examination:

A 2×2 mm sized milky white nodule was retrieved from the right hind leg near the sciatic nerve of mouse#7. This corresponds with the injection of three plates of ES 22.C. A 1×1 mm sized milky white nodule was identified within the muscle tissue of mouse#9 which corresponds with the injection of the three plates of ES 25.F.

Histologic Analysis:

Mouse#7: Histologic sections of the teratoma were analyzed with hematoxylin and eosin (H&E), safranin-O and immunocytochemistry using is cytokeratin (AE1/AE3) and alpha smooth muscle actin antibodies.

H&E: The injected cells formed a round tissue mass within the skeletal muscle tissue. The teratoma consisted of four different sized compartments with cellular debris in the center. Tissue formation was noted on the wall of each compartment (data not shown). Epithelial (round nuclei) and stromal cells (spindle-shaped nuclei) were observed in the teratoma tissue (data not shown). There was no evidence of cartilage, bone or adipose tissue.

Safranin-O: Negative staining was obtained, which indicates the absence of cartilage tissue formation.

Immunocytochemistry with AE1/AE3 antibodies: The teratoma section showed positively stained epithelial cells (data not shown).

Immunocytochemistry with alpha smooth actin antibodies: Small islands of positively stained muscle tissue was observed within the teratoma (data not shown). The retrieved tissue demonstrated epithelial, smooth muscle and stromal tissue components. Cartilage, bone and adipose tissues were not identified in the teratoma.

Mouse#9: Histologic analysis on the retrieved nodule demonstrated a skeletal muscle mass. Microscopic examination showed that no other tissues formed.

EXAMPLE 3

To realize the full potential of therapeutic cloning, it will be important to reconstitute more complex tissues and organs in vitro. Although cloning would eliminate or greatly alleviate the most critical problem—immune compatibility—there is still the task of putting the cells together to create or recreate functional structures.

For example, myocardial infarction is one of the most common diagnoses occurring in hospitalized patients in western countries. While injection of individual or small groups of cardiomyocytes could aid in the treatment of some localized infarcts, this approach is unlikely to be of value in patients with more extended ischemic injury, where the risk of scar formation, cardiac rupture and other complications is much greater. Tissue engineering offers the possibility of organizing the cells into three-dimensional myocardial "patches" which could be used to repair the damaged portions of the heart. For myocardium and other relatively simple tissues, such as skin and blood vessel substitutes, this may involve seeding cells onto masses or sheets of polymeric scaffold. Creating more complex, vital organs, such as the kidney, liver, or even an entire heart will require assembling different cell types and materials in greater combinatorial complexity.

To engineer tissues for use in the animal model, bovine inner cell mass/embryonic discs/stem cells may be generated as described above, and injected into the rear leg muscles of nude or SCID mice. Seven to eight weeks after injection, the resulting teratomas are removed and various cell types are isolated and grown in culture. A number of tissues may be generated from the cloned cells, including smooth and/or skeletal muscle, sheets or "patches" of cardiomyocytes, elastic cartilage, skin, (including the placement of hair follicles), and kidney, including miniature kidneys that excrete urine. These tissues/organ constructs are then transplanted back into the original adult animal from which the donor cell biopsy was obtained.

The following data demonstrates that tissues isogenic for nuclear DNA and allogeneic for mitochondrial DNA form stable transplantation grafts that do not illicit an immune response in the nuclear transfer host. This supports the utility of such cloned cells and tissues for many medical applications, which is quite surprising given the cytotoxic T cell response to mitochondrial antigens observed in different species of mice in response to mitochondrial histocompatibility antigens.

Cell Culture and Seeding

Cells from bovine kidney, heart, skeletal muscle, cartilage and skin were harvested from cloned and allogenic (control) 40 day old fetuses, and expanded separately in vitro.

Kidney:

The kidney tissue was cut into small pieces (1 mm$^2$) using sharp tenotomy scissors. The kidney tissue fragments were digested using collagenase dispase (1 mg/ml) at 37° C. for 30 minutes. The recovered cells were washed with phosphate buffered saline and plated in culture dishes. The cells were grown in medium consisting of DMEM, HEPES 3.1 g/l, Pen/Strep (5 ml/500 ml), L-glutamine 146 mg/L and FBS 10% (Sigma, St. Louis, Mo.).

Muscle:

Cardiac and skeletal muscle cells were processed by the tissue explant technique using Dulbecco's Modified Eagle's Medium (DMEM; HyClone Laboratories, Inc., Logan, Utah) supplemented with 10% fetal calf serum. The cells were incubated in a humidified atmosphere chamber containing 5% $CO_2$ and maintained at 37° C. Both muscle cell types were expanded separately until desired cell numbers were obtained. The cells were trypsinized, collected, washed and counted for seeding.

Polymers:

Unwoven sheets of polyglycolic acid polymers (1×2 cm) were used as cell delivery vehicles. The polymer meshes were composed of fibers of 15 μm in diameter and an interfiber distance between 0–200 um with 95% porosity. The scaffold was designed to degrade via hydrolysis in 8–12 weeks. The polymers were sterilized in ethylene oxide and placed under sterile conditions until cell delivery.

Implantation

Athymic Mice:

To determine whether cells obtained from fetal bovine tissue would form tissue in vivo, cardiomyocytes, skeletal muscle cells and chondrocytes seeded on polymer scaffolds were implanted in the dorsal subcutaneous space of athymic mice. The animals were sacrificed at 1 week, 1 month and 3 months after implantation for analyses (n=4).

Steer:

Each cell type was seeded separately onto polyglycolic acid polymers (1×2 cm) at a concentration of 50×10$^6$ cells/cm$^3$ (n=4 per cell types). The cell-polymer scaffolds were implanted into the flank subcutaneous space of the same steer from which the cells were cloned. The cells obtained from the control (nuclear allogeneic) fetuses were implanted on the contralateral flank of the steer. All implants were retrieved after 6 weeks for analysis.

Analyses

Implantation in Athymic Mice:

Five micron sections of formalin fixed paraffin embedded tissue were cut and stained with hematoxylin and eosin (H&E). Immunocytochemical analyses were performed using specific antibodies in order to identify the cell type of the retrieved tissues. Histochemical analyses using aldehyde fuschin-alcian blue, and immunocytochemical studies using monoclonal anti-collagen II (Chemicon, St. Louis, Mo.) were used to identify the engineered cartilage structures. Monoclonal sarcomeric tropomyosin (Sigma, St. Louis, Mo.) and troponin I (Chemicon, Temecula, Calif.) antibodies were used to detect skeletal and cardiac muscle fibers, respectively. Immunolabeling was performed using the avidin-biotin detection system. Sections were counterstained with methyl green.

Implantation in the Steer:

Immunocytochemical and Histological Analyses:

Five micron sections of formalin fixed paraffin embedded tissue were cut and stained with hematoxylin and eosin (H&E). Immunocytochemical analyses were performed using specific antibodies in order to identify the cell type of the retrieved tissues. Histochemical analysis using Periodic Acid Schiff (Sigma, St. Louis, Mo.), and immunocytochemical studies using polyclonal anti-alkaline phosphatase and anti-osteopontin (Chemicon, Temecula, Calif.) were used to identify renal cells. Monoclonal sarcomeric tropomyosin (Sigma, St. Louis, Mo.) and troponin I (Chemicon, Temecula, Calif.) antibodies were used to detect skeletal and cardiac muscle fibers, respectively. Aldehyde fuschin-alcian blue and monoclonal anti-collagen II (Chemicon, St. Louis, Mo.) were used to stain cartilage tissue implants. Anti-cytokeratins 5/6, AE1/AE3 were employed in order to identify keratinocytes. Bronchial ciliary antibodies were used in order to detect respiratory epithelium. Anti-CD6 antibodies were used in order to identify immune T and B cells. Immunolabeling was performed using the avidin-biotin detection system. Sections were counterstained with methyl green.

Results

The cells grew to confluence, were implanted in the animals with the polymer scaffolds, and retrieved without complications. At retrieval, the implants maintained their initial size without any evidence of fibrosis.

Implants Retrieved from the Steer:

Histochemical and Immunocytochemical Analyses:

Histological examination demonstrated extensive vascularization throughout the implants and the presence of multinucleated giant cells were observed surrounding the polymer fibers. However, higher number of inflammatory cells were present throughout the control allogeneic scaffolds. Histomorphomeric analysis of the explanted tissue (i.e., kidney, skeletal, heart, chondrocytes and keratinocytes) indicated that there was a statistically significant ($p<0.05$; student's t-test) increase in lymphocytic infiltration of the control implants/constructs (non-cloned) versus the cloned tissue types (data not shown). This data suggests that the control grafts were undergoing early graft rejection.

Engineered Kidney Tissue:

Histologically, glomeruli-like structures were observed in the retrieved scaffolds (data not shown). Histochemical analyses using periodic acid schiff identified renal tubular cells (data not shown). Immunocytochemical studies with alkaline phosphatases antibodies confirmed the presence of proximal tubular cells. Studies using osteopontin antibodies were negative in the bovine tissue system.

Engineered Muscle Tissue:

Retrieved cardiac and skeletal muscle cell implants showed spatially oriented muscle fibers in each instance (data not shown). Immunocytochemical analysis using tropomyosin antibodies identified skeletal muscle fibers within the construct (data not shown). Anti-troponin I stained cardiac muscle fibers positively (data not shown).

To prove that the mtDNA of the cloned tissues was from the recipient oocyte, the mtDNA of the nuclear donor and that of the cloned embryo were sequenced. Sequence data confirmed that the mtDNAs were indeed different, particularly in the d-loop region where there were four different corresponding nucleotides in the cloned tissues in comparison with the nuclear donor.

EXAMPLE 4

The above results suggest that it is possible to generate cloned tissues for transplantation by nuclear transfer into an allogeneic background, and that differentiated cells and tissues isolated or constructed from cloned teratomas or cultures of embryonic cells can be transplanted back into the donor animal without significant signs of rejection. To further confirm that nuclear transfer technology has the potential to eliminate the immune responses associated with the transplantation of cells and organs despite mitochondrial mismatch, the inventors will next perform transplants between full grown clones having different mitochondrial backgrounds.

For these experiments, two groups of animals were assembled to test reciprocal skin grafts: (1) four cloned cows (animals CL53-8, CL53-9, CL53-10, and CL53-11) at Trans Ova and (2) five cloned goats at LSU. To perform the test, reciprocal skin grafts (approximately 2–3 cm diameter) are exchanged between the two groups of animals. Self-grafts will serve as positive controls, whereas grafts from genetically unrelated animals will serve as negative controls. The grafts are monitored for signs of immune rejection, and will be removed if and when they become necrotic and the sites patched. If rejection is observed, second-set grafts would then be transplanted in order to confirm the results, which should be rejected in an accelerated fashion.

All of the cloned cows and all of the cloned goats carry the same nuclear genome. However, since mtDNA is transmitted by maternal inheritance, we predict the animals are in fact genetic chimeras with different oocyte-derived mitochondria (this has already been documented in a number of cloned animals). Experiments are underway to obtain the sequence of the mtDNAs from all involved individuals, so that polymorphisms which "segregate" in these panels of animals may be readily correlated with the survival/rejection of skin grafts. If there is a correlation, in vitro assays will be performed to identify target peptides, and the associated mtDNAs which encode the peptides will be isolated.

The experiments aimed at determining mitochondrial DNA polymorphisms will also reveal information about chimerism levels in mtDNA in general. For instance, once the sequences of the mtDNAs are known, a region of maximal polymorphism will be selected, most likely the D-loop, and this segment will be amplified and cloned. A range of clones may then be sequenced to the determine extent of variation in this region. With the mtDNA sequences from a sufficient number of nuclear clones that are allogeneic for mitochondria, an accurate estimate of the levels of chimerism may be determined. Blood samples will also be collected at intervals to carry out various immunological assays. For histocompatibility, standard MLCs and CMLs will be run within the panels and with allogeneic cells.

Discussion

As shown by the data provided above, the present invention demonstrates that it is possible to obtain cloned differentiated cells and tissues for the purpose of tissue engineering and transplantation. The present invention also demonstrates that stable grafts can be achieved with nuclear transfer-generated cloned cells having allogeneic mitochondria, despite the fact that transplantation rejection would be expected due to foreign mitochondrial peptides. In view of the Mta system in mice and similar systems identified in rats, it is surprising that the bovine tissues engineered using the present methods were not rejected when they were transplanted back into the nuclear donor.

There could be several reasons why transplant rejection was not observed with the cloned tissues of the present invention. Without being bound by any particular theory, one hypothesis is that the particular MHC molecules in rodents that present the Mtf, MiHA and other mitochondrial antigens have evolved out of higher mammals. Indeed, H-2M3a, the mouse class I molecule that presents the Mtf and MiHA peptides, is encoded by the M3 gene at the telomeric end of the H-2 complex on mouse chromosome 17 (Fischer Lindahl et al., "Maternally transmitted antigen of mice: a model transplantation antigen," Annu. Rev. Immunol. 1991;9:351–72). Although many genes in this area of the chromosome are conserved between mouse and human, for instance, the MHC class I genes in this region appear to have diverged and evolved independently between species (Jones et al., 1999, "MHC class I and non-class I gene organization in the proximal H2-M region of the mouse," *Immunogenetics* 49(3): 183–95). In fact, the H2-M region is rich in L1 repeats, which some have hypothesized is associated with evolutionary flexibility (Yoshino et al., 1997, "Genomic evolution of the distal MHC class I region on mouse chromosome 17," *Hereditas* 127(1–2): 141–8).

Alternatively, perhaps additional mechanisms evolved in higher mammals which regulate the immune reaction to mitochondrial antigens in the context of MHC, particularly seeing as many aging but otherwise healthy tissues in humans have been shown to contain mitochondrial age-related mutations (Soong and Arnheim, 1995). The ongoing experiments described in Example 4 will be especially useful for identifying the polymorphims that exist in a given population of mtDNAs, and may serve as a useful model system for identifying the changes that occur in mtDNAs over time that may lead to the aberrant display and recognition of mitochondrial antigens.

In any case, despite what was known and understood about rodent mitochondrial histocompatibility prior to the present invention, the results achieved with the therapeutic cloned bovine tissues described herein would predictably translate to other ungulates and higher mammals. Thus, the present invention confirms the therapeutic utility of nuclear transfer-generated cloned tissues in the context of transplantation. Further, by providing a model for testing the immune compatibility of allogeneic and xenogeneic mitochondrial proteins in an isogenic nuclear background, the present invention paves the way for deciphering the immune regulatory systems that exist in and between mammals, which contribute to mitochondrial stability and the separate evolution of species.

What is claimed:

1. A method of testing the immune compatibility of cloned cells or tissues in a non-human mammal model, comprising:
   a. obtaining a donor cell from a non-human donor mammal;
   b. removing the nuclear DNA from a recipient oocyte, transferring the nucleus from said donor cell into the recipient oocyte to form a nuclear transfer unit, activating the nuclear transfer unit and culturing the nuclear transfer unit under conditions that result in the generation of a non-human embryo;
   c. isolating an embryo having at least one cell, an embryonic disc or a stem cell from said non-human embryo;
   d. injecting said embryo, embryonic disc, or stem cell into said non-human donor mammal at the same time as a control embryonic disc or stem cell; and
   e. examining the injection site for teratoma formation and signs of rejection of the injected cells, or of teratomas derived therefrom, to test the immune compatibility of the cloned cells or tissues.

2. The method of claim 1, wherein said cell from said donor animal is transfected with a heterologous gene prior to nuclear transfer.

3. The method of claim 1, wherein said donor and control embryonic discs or stem cell are injected subcutaneously, or into the paralumbar fascia.

4. The method of claim 1, wherein said teratoma, if formed, is removed and examined for the presence of germ layers.

5. The method of claim 4, wherein the germ layers, if formed, are separated for the purpose of detecting or isolating specific cell types.

6. The method of claim 1, wherein the cell obtained from said donor animal is a fibroblast.

7. The method of claim 2, wherein said heterologous gene is a reporter gene selected from the group consisting of green flourescent protein (GFP), beta-galactosidase, and luciferase.

8. A method to evaluate potential developmental signals that control cell differentiation comprising:
   a. obtaining a donor cell from a non-human donor mammal;
   b. removing the nuclear DNA from a recipient oocyte, transferring the nucleus from said donor cell into the recipient oocyte to form a nuclear transfer unit, activating the nuclear transfer unit and culturing the nuclear transfer unit under conditions that result in the generation of a non-human embryo;
   c. isolating an embryo having at least one cell, an embryonic disc or a stem cell from said non-human embryo;
   d. injecting said embryo, embryonic disc, or stem cell into said non-human donor mammal to form a teratoma;
   e. removing the teratoma, and examining the teratoma for the presence of germ layers;
   f. separating the germ layers cells and using the cells in assays to evaluate potential developmental signals that control cell differentiation.

9. A method of engineering a tissue, comprising:
   a. obtaining a donor cell from a non-human donor mammal;
   b. removing the nuclear DNA from a recipient oocyte, transferring the nucleus from said donor cell into the recipient oocyte to form a nuclear transfer unit, activating the nuclear transfer unit and culturing the nuclear transfer unit under conditions that result in the generation of a non-human embryo;

c. isolating an embryo having at least one cell, an embryonic disc or a stem cell from said non-human embryo;

d. injecting said embryo, embryonic disc, or stem cell into said non-human donor mammal to form a teratoma;

e. removing the teratoma, and examining the teratoma for the presence of germ layers;

f. separating the germ layer cells, if present, and using said cells to engineer a tissue.

10. The method of claim 9, wherein said engineered tissue is transplanted back into said donor animal to test immune compatibility.

11. The method of claim 9, wherein said engineered tissue is selected from the group consisting of smooth muscle, skeletal muscle, cardiac muscle, skin, kidney and nervous tissue.

* * * * *